United States Patent [19]

Knowles

[11] Patent Number: 4,955,875
[45] Date of Patent: Sep. 11, 1990

[54] CATAMENIAL APPLIANCE

[76] Inventor: Charlene G. Knowles, 1216 Pear Orchard Rd., Elizabethtown, Ky. 42701

[21] Appl. No.: 300,817

[22] Filed: Jan. 23, 1989

Related U.S. Application Data

[63] Continuation-in-part of Ser. No. 96,514, Sep. 11, 1987, Pat. No. 4,799,929, which is a continuation-in-part of Ser. No. 948,104, Dec. 31, 1986, abandoned, which is a continuation-in-part of Ser. No. 723,466, Apr. 15, 1985, abandoned.

[51] Int. Cl.$^5$ ............................................. A61F 5/44
[52] U.S. Cl. .................................................. 604/331
[58] Field of Search ............... 604/331, 330, 328, 329, 604/358, 317, 319

[56] References Cited

U.S. PATENT DOCUMENTS

| | | | |
|---|---|---|---|
| 1,682,266 | 8/1928 | Daggy | 604/331 |
| 1,743,733 | 1/1930 | Spardel | 604/331 |
| 2,182,702 | 12/1939 | Previn | 604/331 |
| 2,915,065 | 12/1959 | Lyons et al. | 604/331 X |
| 3,037,508 | 6/1962 | Friedman . | |
| 3,128,767 | 4/1964 | Nolan . | |
| 3,216,422 | 11/1965 | Steiger et al. . | |
| 3,983,874 | 10/1976 | Davis et al. . | |

Primary Examiner—John D. Yasko
Attorney, Agent, or Firm—Middleton & Reutlinger

[57] ABSTRACT

Catamenial appliance having an outwardly spring biased flexible ring insertable into the vagina of a female and over the cervix, attached to a closed collecting sheath to contain and direct menstrual flow. The collecting sheath protrudes only slightly from the vagina yet will still permit total intra-vaginal containment of menses. In alternate embodiments, the distal end may be provided with means to permit emptying of menses without removal of the ring and sheath.

4 Claims, 5 Drawing Sheets

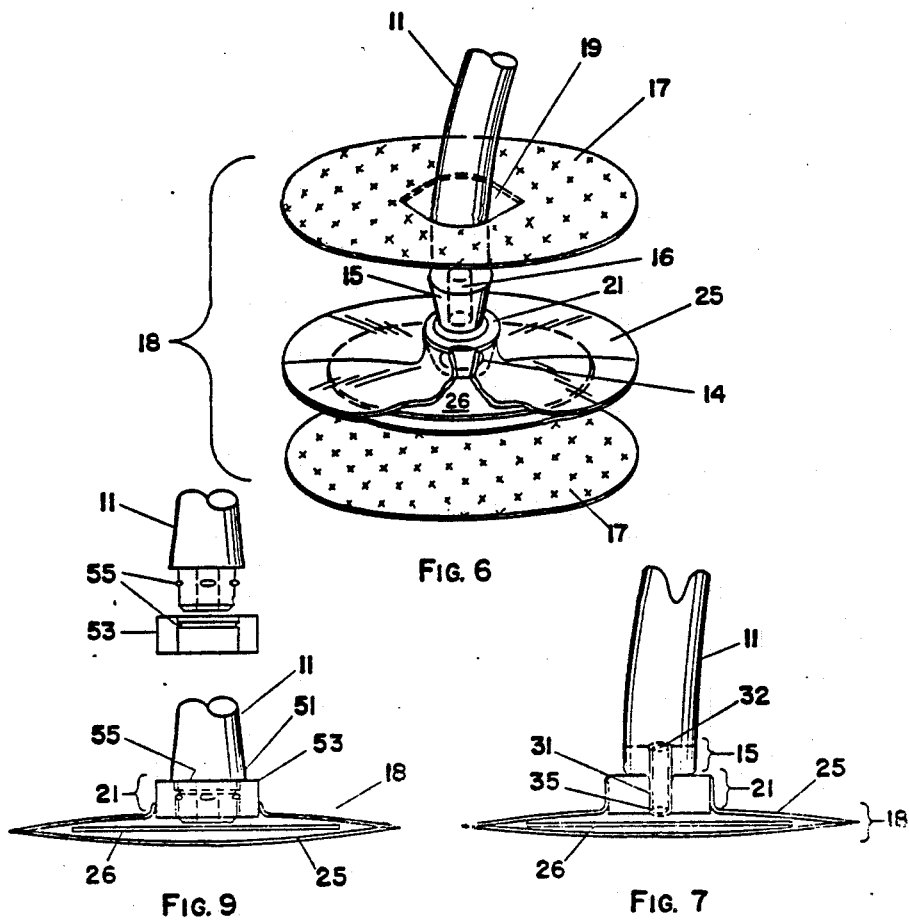
FIG. 6
FIG. 9
FIG. 7
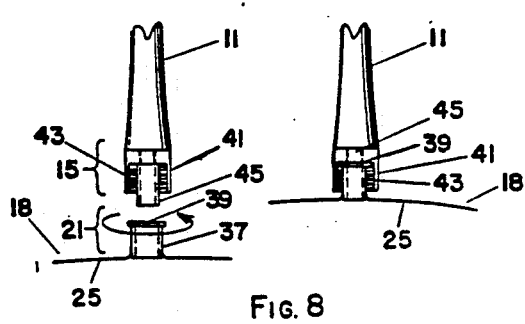
FIG. 8

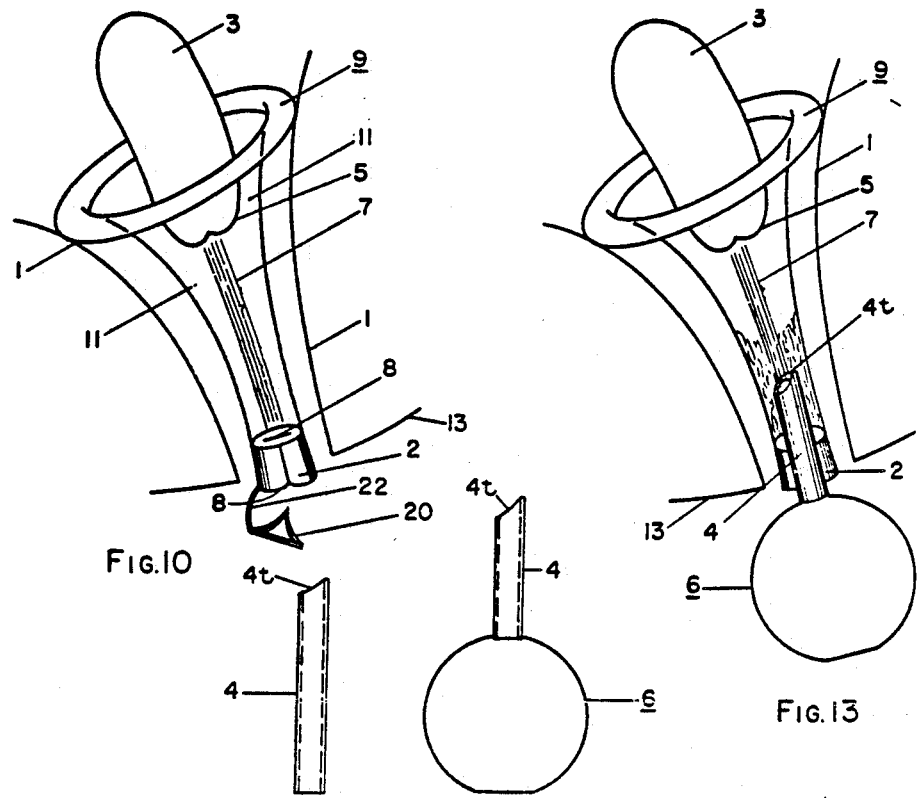
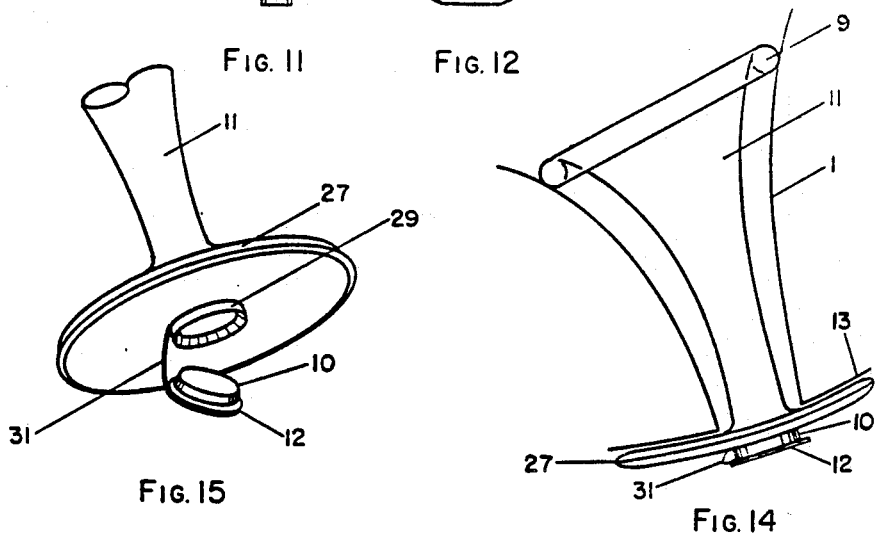

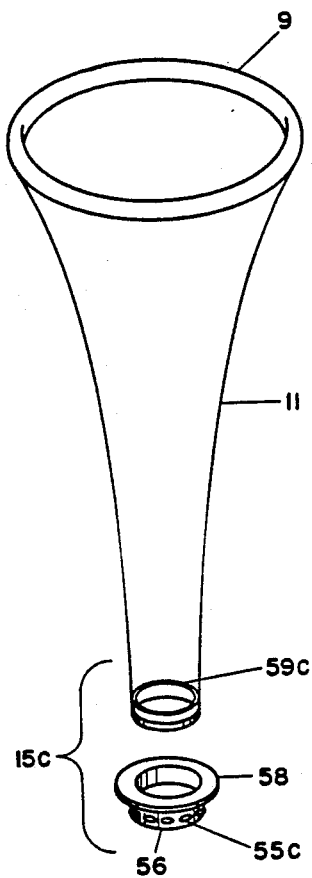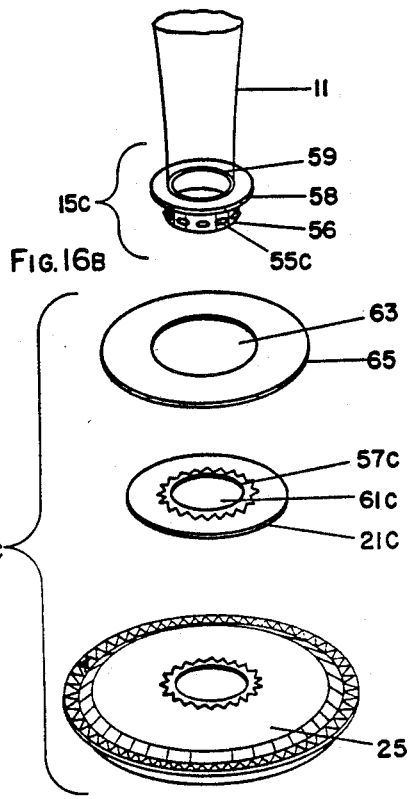

CATAMENIAL APPLIANCE

This is a Continuation-In-Part of my prior-filed application, Ser. No. 07/096,514 now U.S. Pat. No. 4,799,929, filed 9/11/87 (the disclosure of which is incorporated herein by reference), which is a continuation-in-part of Ser. No. 06/948,104, filed 12/31/86 now abandoned; Ser. No. 06/948,104 in turn is a Continuation-In-Part of Ser. No. 06/723,466 filed 4/15/85, now abandoned.

The present invention, described more particularly herein below, relates to a new and improved catamenial appliance having, in one embodiment, a detachable and water-degradable and flushable collector having a leak-proof internal reservoir to contain menstrual flow, designed to be used in comfort while providing complete containment of menses flow. In another embodiment, a self collector cap and port means may be substituted for the collector pouch. In another embodiment, the catamenial appliance is provided with a closed-end collecting sheath for complete intra-vaginal containment of menses. In another embodiment, the distal end of the collecting sheath is provided with selectively-separable interruptible means to contain menses flow within the sheath. In this latter embodiment, the catamenial appliance may be contained totally within the vaginal space of the user. In another embodiment, the appliance is provided with a self-lip cap, providing complete ease of connection between the collecting sheath and collector pouch containing the internal reservoir.

BACKGROUND AND NECESSITY OF THE INVENTION

Presently available catamenial appliances are generally of two types, described in the trade as either the tampon or the sanitary napkin. Use of either means involves significant discomfort and performance shortcomings. The Tampon generally consists of a vaginally inserted collection pad, but a tampon has a limited absorption capacity, requiring frequent changes during menstruation to prevent leakage and/or staining of the user's clothes. In addition, tampons have been linked as a cause of toxic-shock syndrome. Sanitary napkins are worn against the vulva outside the body, but it is difficult to prevent movement of a sanitary napkin (especially during activity), thereby also raising the distinct possibility of a leak or stain of menses fluid. Like tampons, the presently available sanitary napkins require frequent changes during a given menstrual period, which of course must be conducted in private. Given the unpredictability of menses production when combined with the limited absorption capacities of both presently known means, it is never quite possible to predict when such privacy will be required. If a change is needed when privacy is not available, this results in uncomfortable and annoying leaking to the user. The sanitary napkin has the additional disadvantage of often creating (or at least not masking) an offensive odor during menses flow. In addition, both means are uncomfortable to the user and require restriction of activities to permit them to function as well as their respective limitations will permit.

The present invention, hereinafter described, avoids the disadvantages of bulk and discomfort, limited absorption capacity, limitation of activities, and the necessity of excessive intra-vaginal insertions to effectuate changes of tampons.

Basically, the present invention consists of a flexible spring-biased ring insertable over the cervix in combination with a permanent sheath attached to the flexible ring and shaped to collect menses fluids from the uterus and direct them downwardly toward the distal end of the sheath. The distal end of the sheath is closed, thereby containing menses within the sheath, which may be composed of water-degradable biodegradable leak-proof material. The sheath is designed so that when it is in place, the distal end does not protrude externally from but is easily accessible by the user from the vagina, so as to permit the user to easily change the sheath as desired. In an alternate embodiment, the distal end of the collector sheath is provided with means to permit emptying without removal of the sheath from the cervix.

Use of present invention will permit the user total menses containment during menstruation, by simple insertion of the sheath onto the cervix at the commencement of menstruation, and removal at the completion of the period or any time prior thereto at the convenience of the user. In use, the present invention would not restrict the user's activity level, as movement of the device would not cause a leak, since the flexible ring around the cervix and the distal end of the sheath, the only possible sources of any leaks, would be quite stable. The present invention also is an improvement over the sanitary napkin, in that because the ring is inserted directly over the cervix, there is complete containment of menstrual flow from the time it leaves the uterus.

A primary object of the present invention is to provide an economical catamenial appliance capable of complete containment of menstrual flow, instead of having to deal with over-saturated sanitary napkins or tampons, which can cause uncomfortable moisture, unpleasant odors, and staining. The capacity of the present invention's internal sheath to contain menses flow is significantly increased over presently available devices. That increased capacity will provide complete containment of menstrual flow, allowing the user the freedom to wear the present invention for many hours, instead of having to change every one or two hours to avoid overflow.

Another object is to provide a leakproof catamenial device that would control and contain menstrual flow as opposed to the leaking and staining associated with tampons and napkins. This complete control and containment of menstrual flow would eliminate the need for the user to have a supply of replacement tampons or sanitary napkins.

A final purpose is to provide a non-bulky, leakproof catamenial device to fit completely within the user's vulvar space to permit the user to engage in swimming and other sports during menses.

Reference to the following description will reveal to those skilled in the art other objects and purposes within the scope of the present invention.

BRIEF DESCRIPTION OF THE DRAWINGS

FIG. 6 is an exploded side view partially broken away of the collector pouch assembly; and FIGS. 7, 8 and 9 are schematic side sectional views of alternate connecting means to connect the distal end of the collecting sheath to the collector pouch;

FIG. 10 is a schematic view showing another embodiment of the present invention, which can contain menses in the collecting sheath totally intra-vaginally, or with only slight protrusion;

FIG. 11 shows one of the emptying devices for the embodiment disclosed in FIG. 10;

FIG. 12 shows another emptying device, such as a suction bulb, which may remove menses from the collecting sheath;

FIG. 13 is a schematic view of the embodiment disclosed in FIG. 10 being emptied of collected menses by means of the suction bulb;

FIG. 14 is a schematic view of another embodiment of the present invention, whereby access to collected menses within the collecting sheath is obtained by a recloseable cap and port, attached to the distal end of the sheath, and FIG. 15 is a broken away perspective view of the distal end of the collecting sheath, showing and the recloseable cap and port.

FIG. 16A is a schematic exploded perspective view of another embodiment of the ring, sheath, and connector means incorporating a self lip connector to even more facilitate the connection between the collecting sheath and the collector pouch assembly;

FIG. 16B is a schematic broken away prospective view which shows the self-lip connector after it has been affixed to the distal end of the connecting sheath;

FIG. 17 is an exploded perspective of the collector pouch assembly which has been adapted to accommodate the self-lip connector.

DETAILED DESCRIPTION OF PREFERRED EMBODIMENT

Figure 1:
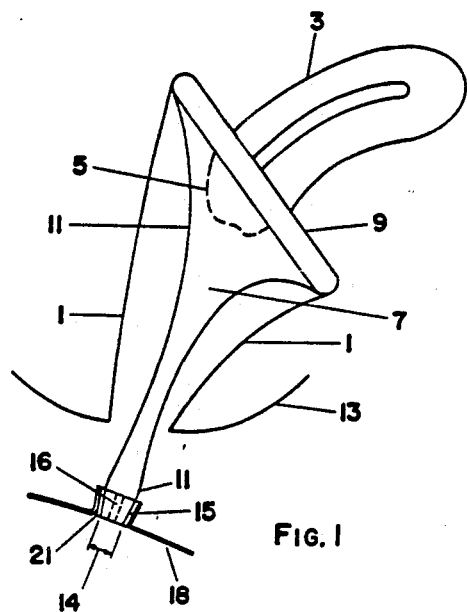
FIG. 1 is perspective a view showing the present invention in place, with a flexible ring end of the collecting sheath surrounding the cervix, with a closed distal end.

FIG. 1 shows the device as it lies in place within the vaginal walls (1). The uterus (3) and cervix (5) are shown to indicate where menstrual flow (7) begins. The containment of this menstrual flow is initiated by the flexible ring (9) which is shown surrounding the cervix (5). The flexible ring is similar to the known contraceptive device known as the diaphragm. The flexible ring (9) does not require sizing by a physician, and may be placed in position by the user, either using an inserting device or her fingers.

Attached to the flexible ring (9) is a collecting sheath (11) which continues to contain and direct menstrual flow downwardly through the vagina and toward the line of the vulva (13). The collecting sheath (11) of the present device is conical in shape and is somewhat similar to the device described in U.S. Pat. No. 2,915,965, W. C. Lyons, et al. The sheath is made of any suitable material, such as silicone, polyvinyl alcohol or a thermoplastic. The sheath would protrude from the vulva, an optimum amount, to permit attachment or detachment of the leakproof collector pouch as hereinafter described.

A hollow durable male annular connector (15) with a central bore (16) therethrough is attached to the distal end of the collecting sheath (11). The annular connector (15) lies outside the body. The shape of the connector (15) is generally conical with the diameter of the top circumference being larger than the diameter of the lower (distal) circumference. The diameters of the top and lower circumference would be, for example, 9/16" and 7/16" respectively. The connector (15) has an opening (16) therethrough from top to bottom, with the opening having an inside diameter of, for example 5/16" to permit free flow of menstrual fluid. The height of the connector (15) would be for example 5/16." The conical connector (15) is attachable and detachable) into hollow semi-firm cylindrical female connector (21), also provided with a central bore (14) therethrough. The connection between (15) and (21) is described more fully below.

Figure 2:
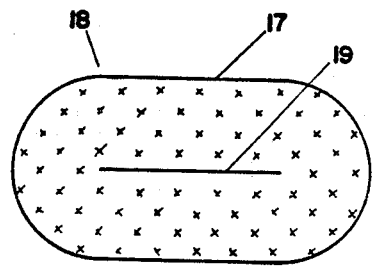
FIG. 2 is an anterior view of the detachable collector pouch of the present invention.

FIG. 2 discloses how the present invention is provided with detachable, outside-the-body collector pouch (18), shown in detail in FIG. 6. The collector pouch includes upper and lower layers of collector padding (17), with the upper having split top layers (19). When the split top layers (19) are pulled apart a disposable annular female connector (21) of the collector pouch (18) is exposed. This female connector (21) is described in more detail in FIG. 3. The padding (17) and the split top layers (19) will give protection to the vulva from the connection between the male annular connector (15) and the female connector (21), but will also allow continuous patency of the collecting sheath (11). In FIG. 6, the leakproof collector pouch (18) is shown generally in an oval configuration for disclosure purposes but may advantageously be provided in any number of other shapes. The detachable collector pouch assembly may be non-flushable or water-degradable and flushable. If non-flushable, the collector pouch assembly (18) is constructed of any suitable non-leaking materials similar to those used in presently known sanitary napkins.

A leakproof reservoir (25) (See, FIG. 6) is incorporated within the collector pouch (18). The collector pouch (18) which includes the reservoir (25), the padding (17) and the connector (21) can be commode-flushable using materials which are readily degradable in water and also biodegradable. The components of the collector pouch (18) are shown in more detail in FIG. 6. A comfort-providing feature of the present invention is that the collector pouch (18) size is considerably smaller than the present day sanitary napkin pads. As an example, the collector pouch (18) is 3" long and 2" wide and would only be as thick as necessary to hold approximately 1½ to 2 ounces of menstrual flow in the reservoir, for example, approximately ⅜". The user would thus be assured that the outline of the collector pouch (18) would not be observable under tight clothing.

Figure 3:
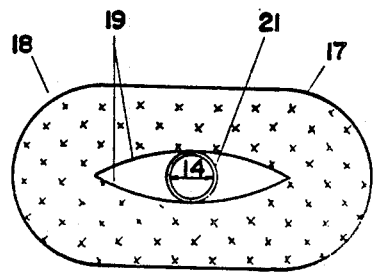
FIG. 3 is another anterior view of the collector pouch showing how the split top layers of the collector padding are molded around the connecting means of the collector pouch assembly.

FIG. 3 discloses the split top layers (19) of the padding (17) of the collector pouch as pulled apart to reveal the disposable annular female connector (21) designed for connection with male connector (15) of the distal end of the sheath (11). The connector (21) is a cylindrical in shape with a central bore (14) therethrough. The central bore (14) is alignable with central bore (16) of connector (15). For example, central bore (16) may be 5/16," and central bore (14) may be "7/16" or "½." The outside diameter of connector (21) is, for example, 10/16." The inside diameter of the bore (14) is sized to permit a firm fit with the conical male connector (15), this measurement of bore (14) being, for example, 8/16." The connector (21) allows a firm connection with connector (15), and can be degradable in cold water. The action of degrading would take place in a commode after the collector pouch (18) is removed from the distal end of the sheath (11) by disconnecting connectors (21) and (15), and the collector pouch (18), designed for flushing, is disposed of in the commode.

A pressed-paper product, commonly available from such manufacturers as Jonesville Paper Tube Co., Jonesville, Mich., is suitable for the connector (21). The surface of the inside diameter of (21) could also contain an adhesive to enhance the gripping and/or holding of connector 15, to ensure a firm connection between connectors (21) and (15).

The connection of the female connector and the male connector (15) would be effected by pressing until the outside circumference of connector (15) is seated firmly with the inside diameter of connector (21). Menses flows from the collecting sheath (11) through the central bores (14) and (16) of the reservoir (25) of the collector pouch (18). The releasing of connectors (15) and (21) is easily effected by a twisting, pulling motion applied outside the body to the collector pouch.

Figure 4:
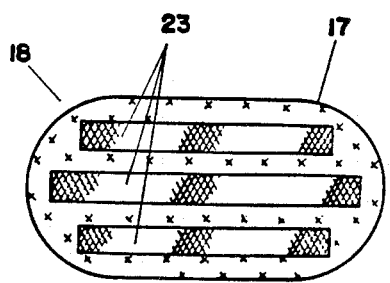
FIG. 4 is a posterior view of the collector pouch showing adhesive strips which will adhere to a snug panty to hold the collector pouch securely in the vulvar space during use.

Reference to FIG. 4 shows that the collector pouch (18) may be equipped with any number of adhesive strips (23) placed in any design on its bottom surface. The user would press these strips (23) firmly against a snug panty. This would keep the leakproof collector pouch (18) securely in place in the vulvar space during activity.

Figure 5:
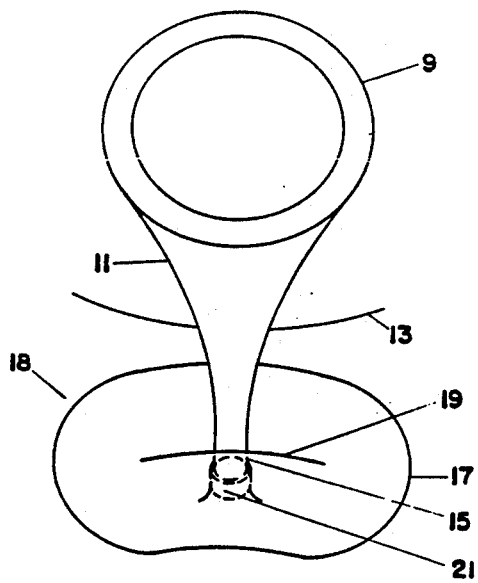
FIG. 5 is a perspective view of all the components of the present invention.

In use, FIG. 5 shows the flexible ring (9), the attached collecting sheath (11) with the male connector (15) of the distal end of sheath (11) protruding below the vulva line (13). The completed connection of annular male and female connectors (15) and (21) are shown lying under the split top layers (19) of top padding pad (17) of the collector pouch.

FIG. 6 is an exploded perspective view showing the entire detachable collector pouch, including the split top layers (19) of the top padding (17), the leakproof reservoir (25) and the connectors (15) and (21) and the lower padding. The menses is collected and contained in reservoir (25) until the entire collector pouch (18) is changed. If the non-flushable collector pouch is used, it is disposed of in a container. If the flushable collector pouch is used, it is flushed in the commode. The reservoir (25) can be made of a non (water-degradable or water-degradable materials depending on whether the collector pouch (18) is to be non-flushable or flushable. The non-flushable reservoir (25) is made of a soft, leakproof plastic. the water-degradable reservoir (25) is made of any leakproof, water-degradable, plastic type material such as refined or processed polyvinyl alcohol, as, for example, the material disclosed in U.S. Pat. No. 3,563,244 (asaka). Such materials have the properties of containment of a substance, such as menstrual flow, of degradability when coming in contact with cool water, as, for example, that ordinarily contained in a commode. This water-degradable material is also biodegradable, so such material would be acceptable by municipal sewer and water systems. The water-degradable reservoir (25) may also be provided with absorbent material 26 within its interior to absorb some of the moisture of the menstrual flow as it collects in the reservoir, thereby enhancing the reservoir's property of holding the flow safely. The remainder of the flushable collector pouch (18) is constructed of any soft, absorbent materials such as a short-fibered paper product which is quickly degradable when in contact with water, and is also biodegradable. It should be stated that FIG. 6 shows that component of the collector in disproportionate scale for clarity of disclosure.

FIG. 7 shows an alternative embodiment of the connection between connector (15) and connector (21). Another design of a durable annular male connector (15) is attached to the distal end of collecting sheath (11). The connector (15) is cylindrical rather than conical (as in FIGS. 1 and 6), and has a smaller cylindrical hollow stem (31) with a central bore (32) therethrough projecting downwardly from its lower surface. The stem seats firmly into a bore (35) provided in the connector (21) of the collector pad assembly (18). Bore (35) is alignable with stem (31). Menses will flow through the sheath (11) through the hollow stem (31) through the bore (35) of the connector (21) and into the collector pouch (18). The inside diameter of the hollow stem (31) is adequate to carry menstrual flow, for example, 5/16." The overall size of the connector (15) would be in the same dimensional range as earlier stated. The outside surface of the stem is processed to have optimum holding and gripping ability to assure a firm connection with the inside surface of the bore (35) of connector (21).

Another embodiment to connect the collecting sheath (11) to the collector pouch (18) is disclosed in FIG. 8. This embodiment uses a hollow stem (37) having a threadable tip (39) on the receiving end of the connecting means (21) of the collector pouch (18) which is adaptable to be threaded into a threaded distal end (41) of the collecting sheath (11). The threaded distal end (41) is provided with threads (43) to receive the tip (39) of the hollow stem (37). Menses flows through the threaded distal end to the collector pouch (18) by means of an internal sheath stem (45) which is of selected diameter to be insertable into the inside diameter of hollow stem (37). As with other embodiments, the inside diameter of stems (37) and (45) is sufficient to permit menses to flow therethrough, for example 5/16."

Reference to FIG. 9 discloses a third alternate connecting means (21) to connect the distal end of the collecting sheath (11) to t he collector pouch (18). In this embodiment the connector (15) attached to the distal end of the collecting sheath (11) is cylindrical in shape. It has a central bore (59) therethrough which will carry the menses flow from the collecting sheath (11) into the collector pouch (18). A series of nodules (55) is provided around the outer periphery of connector (15). The dimension of this connector is matched to be receivable into the receiving portion of the connector (21) attached to the collector pouch (18). Connector (21) is also cylindrical with a central bore (61) therethrough which will receive connector (15). A slightly protruding ring (57) is provided around the inner periphery of central bore (61). When connector (15) is pressed into central bore (61) the nodules (55) come in contact with protruding ring (57). The resistance to compression of the connector (21) and the protruding ring (57) is less than the compression resistance of the nodules (55) so that connector (21) is expanded as the nodules are pressed into central bore (61). This expansion allows nodules (55) to proceed beyond protruding ring (57) of central bore (61) and be snapped into connector (21) effecting the connection. When it is desired or required to change the collector pouch assembly, the above procedure is simply reversed.

Use of the present device will be possible without curtailing the user's activities. For example, those who engage in water activities will be able to continue to use the present catamenial device while in the water. A waterproof reservoir without absorbent materials as used in the previously described leakproof collector pouch (18), could be available. This reservoir (not shown) is made of any suitable waterproof material such as plastic or rubber. A waterproof connector (21) is attached to such reservoir. This reservoir and connector (21) is essentially the same as the collector pouch (18), but would be disposed of in a container rather than being flushable. Such reservoir would be retained in place in the vulvar space by the usual tight swim wear and by the firm connection between connector (15) and connector (21).

FIG. 10 discloses another embodiment of my device as it lies within the vaginal walls (1). The cervix (5) is shown to indicate where menstrual flow (7) begins. The containment of menses is initiated by the flexible outwardly-biased ring (9) which is shown surrounding the cervix. Attached to the flexible ring is a collecting sheath (11) which continues downwardly through the vagina and slightly past the vulval line (13). See description accompanying FIG. 1, supra, for further details pertaining to the flexible ring and collecting sheath. A semisolid selectively closable distal end (2) of the collecting sheath (11) protrudes only slightly past the vulval line (13). The distal end is made of any suitable semisolid material such as a liquid filled micro cell sponge which is produced by The 3-M Company. The distal end (2) includes an aperture therethrough (8), which allows for the emptying of menses. This distal end could be any of a variety of shapes, for example, having a diameter of ½" and length of 5/8." A plug (20), insertable into aperture (8), is utilized to retain menses within the collecting sheath (11). This plug (20) would force fit into the distal aspect of aperture (8) of the distal end (2). This plug (20) is attached to the distal end (2) by a thin strand (22) of nylon or any other acceptable material. The plug (20) is made of a material which would provide effective adherence to the material of the distal end (2) but still allow for disengagement for emptying purposes.

FIG. 11 shows one of the possible emptying devices for use with the embodiment described in FIG. 10. In this embodiment, the selectively separable parts of distal end (2) are selected so that aperture (8) is normally closed to retain collected menses within sheath (11). The emptying device is a simple, thin hollow tube (4) made of hard plastic or any other suitable material. The tip (4t) of emptying device (4) would be slanted and smoothed and sized to permit easy and safe insertion into aperture (8) causing separation of the walls of distal end (2) and permitting menses to be emptied through aperture (8) through tube (4). The menses would be emptied from collecting sheath (11) into commode by gravity. The shape of tube (4) would be any suitable dimension, for example, 7/16" in diameter with a bore of 6/16" with a length of approximately 3¼."

FIG. 12 shows an alternate emptying device (6) which is similar to a rubber suction bulb presently known. The insertable tip would be made of hard plastic similar to tip (4t), or any other suitable material and dimensioned to be adaptable for insertion into aperture (8) and would empty menses from the collecting sheath (11) by suction.

FIG. 13 shows how the emptying device (6) is used for emptying menstrual flow. As stated, distal end (2) is selectively separable, malleable and moldable such as, for example, liquid-filled micro cell sponge or any other suitable material, so that the aperture (8) remains sufficiently closed to prevent leakage of menses as it is being collected and thus held within the collecting sheath (11). Distal end (2), being selectively separable, is malleable to allow the tip (4t) of emptying device (4) or (6) to be inserted easily and comfortably into the aperture (8). Estimation of menstrual flow for the entire menstrual period has been 50-150 ml. With this in mind, many hours of menstrual flow would be containable within the collecting sheath until the user could empty it at her convenience.

FIG. 14 discloses another embodiment of the present invention. The flexible sprint type ring (9) lies within the vaginal walls (1) and surrounds the cervix (5). The collecting sheath (11) proceeds downwardly past the vulval line (13) and becomes shaped into a small self-collector (27), show lying within the vulvar space. A recloseable emptying port (29), for the purpose of emptying menstrual flow (7), is on the distal surface of the self-collector. The dimensions of the self collector would be, for example, 2" in length and 1" in width. Any other shapes would be acceptable so long as they achieve the result of permitting access to collected menses. The collecting sheath and molded self-collector is made of any suitable material such as silicone or thermoplastic. These materials are pliable for comfort and physiologically safe yet firm enough to hold any shape. These materials also would allow the user to cleanse the self-collector in her personal hygiene routine.

FIG. 15 is a perspective view of the distal surface of the self-collector (27). A recloseable port (29) is provided for periodically emptying the menstrual flow from the collector. The recloseable port is positioned on the distal side of the collector so that the vulva would be protected from the port itself. The port could be provided in any suitable shape, oval, for example, with a diameter of, for example, ⅝." Any other appropriate emptying means could be employed.

Any other suitable mechanism for closing the port could be used, force fit for example. FIG. 15 shows an oval force fit cap (10) including a self-tab (12). This tab would be easily grasped by the user to open the port for emptying. The closing device (10) is attached to the recloseable port by a thin strand (31) of material such as nylon thread or plastic.

FIGS. 16A and 16B show another preferred embodiment of the connecting means shown in FIG. 9, which has been modified further to facilitate the user in making the connection between male connector (15c) and female connector (21c). The collector pouch is not included in these figures FIG. 16A shows the self-lip connector disconnected from the distal end of the collecting sheath (II), and FIG. 16B shows it connected thereto FIGS. 16A, 16B and FIG. (17) show a flatter connector (15c) provided in the form of a self-lip cap (15c). The purpose of the self-lip is to allow the user to more easily manipulate the connector between male connector (15c) and female connector (21c). A thin but firm inner ring 59c) is provided on the distal end of the collecting sheath (11) to permit the sheath to be engaged into the self-lip cap (15c). Self lip could be oval or round, which of course, is exemplary only. The overall height of connector (15c) is, for example, about 3/16", the thinnest of all disclosed embodiments. The width of the self-lip wings (58) is, for example, about ⅛", which is sufficient for user control. This will optimally allow seating of cap 15c's protruding ring (56) into connector (21c).

The self-lipped collector pouch assembly (18c) is shown exploded in FIG. (17). It is adapted to allow seating of the self-lip cap (15c) to enhance user comfort. This seating of the self-lip permits the connector (15c) to lay virtually flush to the upper surface of the collector pouch assembly and provides a very thin over-all collector pouch assembly. FIG. 17 also shows the lower section of the collector pouch assembly including the collecting portion which incorporates the leakproof internal reservoir (25) which of course is surrounded by outer padding (not shown), as discussed above. This outer padding restricts the reservoir from contacting the user's body and provides comfort to the user. The materials used for this portion of the collector pouch assembly would be the same as described above.

To adapt the collector pouch assembly to receive self-lip cap 15c, the middle portion of the collector pouch assembly is provided with a very thin female connector (21c). It would be made of a paper product similar to that described above, firm enough to withstand several connections and disconnections from connector (15c). The protruding ring (57c) similar to that described in connection with FIG. 9, would accept and retain nodules (55c) of the connector (15c) when the connection is made by force fit. The central bore (61c) of connector (21c) is shown which is adapted to receive the male end (56) of cap (15c). Self-lip cap (15c) is detachably locked into connector (21c) by the nodules (55c) on the outer periphery of the male protrusion (56) of self-lip cap (15c). The middle portion (21c) of the collecting pouch assembly is attached to the lower portion (25) by an adhesive or a heat process, as shown by the dotted lines of FIG. 17; these methods of affixation are well known. To facilitate connection between pouch assembly (18c) and self-lip cap (15c), the pouch assembly (18c) and self-lip cap (15c), the pouch assembly (18c) is provided in a greater diameter than the diameter of wings (58), so that wings (58) fit flush against and are covered by tab (65). Tab (65) of the collecting pouch assembly (18c) is made of firm water-degradable paper, and is affixed to connector (21c) by standard adhesive techniques. Tab (65) is provided with a central cutout (63) to allow the protrusion (56) of self-lip cap (15c) of connector (15c). AS disclosed above, the entire collecting pouch assembly (18c) could be made of water-degradable materials to be flushable in a commode or of materials which could be disposable in a waste container. This collecting pouch assembly could also be made of water-proof materials for the swimmer and would be disposed of in a waste container after use as described above.

Figure 18:
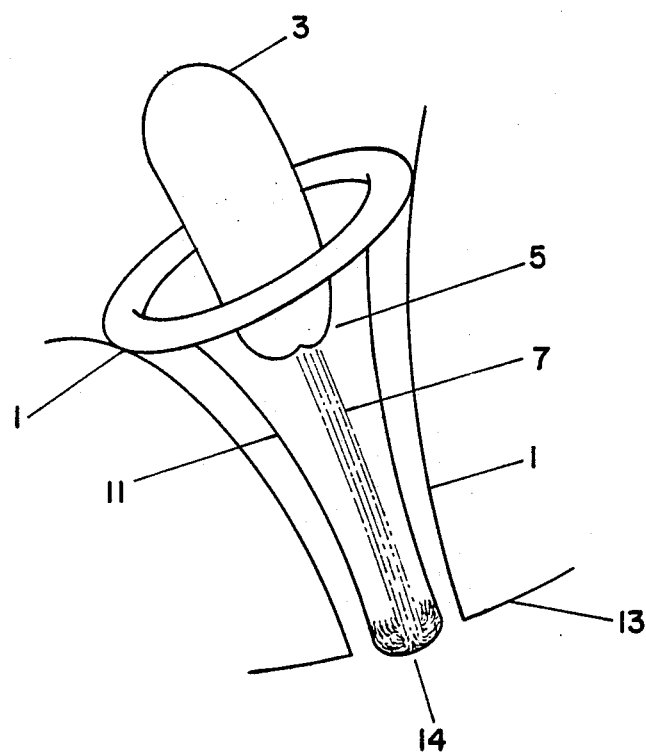
FIG. 18 is a perspective view of an alternate embodiment of the present invention, showing a closed distal end of the collecting sheath.

FIG. 18 discloses another embodiment of the present invention where the distal end (14) of the collecting sheath (as generally described above) is totally closed. In this embodiment, the distal end (14) does not protrude appreciably beyond the vulvar line (13), thereby providing containment of menses substantially within the body. This embodiment would provide the user with the greatest degree of freedom of movement during menstruation, and would still provide the benefits of complete containment. The sheath is designed to contain a sufficient volume of menses such that removal and emptying would only be required every 12 hours or so, thereby providing a total containment within-the-body catamenial appliance. This embodiment can also be provided with access means on the distal end of the sheath to permit emptying of menses without removal of the collecting sheath. See, discussion Related to FIGS. 10–15 above.

The above description should not be construed as limiting the ways in which this invention may be practiced but should be inclusive of many other variations that do not depart from the broad interest and intent of the invention. Also, of course, all dimensions are exemplary only and are not intended and should not be used to limit the scope of the present invention.

I claim:

1. A Catamenial appliance comprising:
flexible ring means insertable into the vagina of a female and adaptable to surround the cervix of said female, said flexible ring means being biased to expand slightly outwardly after insertion over said cervix and having a relatively small cross-sectional area whereby contact with the vaginal walls of said female is limited to a generally narrow band of contact defined by the outer periphery of said small cross-sectional area of said flexible ring means, collecting sheath means attached to said flexible ring means and extending downwardly therefrom to contain and direct menstrual fluids downwardly from said cervix through said vagina of said female, said sheath means at its distal end including a radially extending small self-collector adapted to lie substantially within the vulvar space of said female.

2. The invention of claim 1 wherein said distal end of said collecting sheath is comprised of selectively separable material with an aperture therethrough to permit menstrual fluids to be directed into collecting means and including collecting means adaptable to be inserted into said aperture of said distal end of said selectively separable distal end of said collecting sheath to access menstrual fluids collected within said collecting sheath.

3. The invention of claim 1 wherein said distal end of said collecting sheath is provided with a cap adaptable to be inserted into said aperture of said distal end to prevent menstrual fluids from flowing through said aperture, thereby retaining said menstrual fluids within said collecting sheath.

4. The invention of claim 3 wherein said emptying means is a recloseable cap-and-port means having a tab on said cap of said cap-and-port means to permit the user to open and close said cap-and-port emptying means, and when said cap-and-port emptying means are open to permit said menstrual fluids to flow from said collecting sheath.

* * * * *